United States Patent
Dickenson et al.

(10) Patent No.: US 10,458,224 B2
(45) Date of Patent: Oct. 29, 2019

(54) MONITORING OF EQUIPMENT ASSOCIATED WITH A BOREHOLE/CONDUIT

(71) Applicant: SCHLUMBERGER TECHNOLOGY CORPORATION, Sugar Land, TX (US)

(72) Inventors: Paul Frederick Cilgrim Dickenson, Romsey (GB); Gareth P. Lees, Romsey (GB); Arthur H. Hartog, Romsey (GB); Cheng-Gang Xie, Singapore (GB); Paul Simon Hammond, Cambridge (GB); Ashley Bernard Johnson, Cambridge (GB); Gary Martin Oddie, Cambridge (GB); Andrew William Meredith, Cambridge (GB); Franck Bruno Jean Monmont, Cambridge (GB); Theo Cuny, Romsey (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 260 days.

(21) Appl. No.: 15/115,533

(22) PCT Filed: Feb. 2, 2015

(86) PCT No.: PCT/US2015/014027
§ 371 (c)(1),
(2) Date: Jul. 29, 2016

(87) PCT Pub. No.: WO2015/117051
PCT Pub. Date: Aug. 6, 2015

(65) Prior Publication Data
US 2017/0167245 A1    Jun. 15, 2017

Related U.S. Application Data

(60) Provisional application No. 61/934,614, filed on Jan. 31, 2014.

(51) Int. Cl.
*E21B 47/00* (2012.01)
*G01V 1/40* (2006.01)
(Continued)

(52) U.S. Cl.
CPC ........ *E21B 47/0007* (2013.01); *E21B 43/128* (2013.01); *E21B 47/00* (2013.01);
(Continued)

(58) Field of Classification Search
CPC .... E21B 47/00; E21B 47/0007; E21B 47/042; E21B 47/065; E21B 47/091; E21B 47/123; E21B 43/128
See application file for complete search history.

(56) References Cited

U.S. PATENT DOCUMENTS 7,040,390 B2 * 5/2006 Tubel ................ E21B 23/03
166/250.01
7,668,411 B2   2/2010 Davies et al.
(Continued)

OTHER PUBLICATIONS

Search Report for European Patent Application No. 15743078.6, dated Sep. 18, 2017, 4 pages.
(Continued)

*Primary Examiner* — Jennifer H Gay

(57) ABSTRACT

Monitoring one or more items of equipment associated with a borehole or other conduit. A sensor system includes a vibration sensor for sensing vibrations at one or more sensor locations associated with one or more items of the equipment and/or the borehole or other conduit. A processing system processes the sensor information to determine a
(Continued)

characteristic of the operation of the one or more items of equipment and/or the borehole or other conduit.

52 Claims, 8 Drawing Sheets

(51) Int. Cl.
    *G01V 1/50*           (2006.01)
    *E21B 43/12*         (2006.01)
    *E21B 47/06*         (2012.01)
    *E21B 47/12*         (2012.01)
    *G01N 29/24*        (2006.01)

(52) U.S. Cl.
    CPC .......... *E21B 47/065* (2013.01); *E21B 47/123* (2013.01); *G01N 29/2418* (2013.01); *G01V 1/40* (2013.01); *G01V 1/50* (2013.01)

(56) References Cited

U.S. PATENT DOCUMENTS

| | | | | |
|---|---|---|---|---|
| 7,946,341 | B2* | 5/2011 | Hartog | E21B 43/26 166/254.1 |
| 8,020,616 | B2* | 9/2011 | Greenaway | E21B 47/0007 166/250.01 |
| 8,225,867 | B2 | 7/2012 | Hartog et al. | |
| 8,347,958 | B2 | 1/2013 | Hartog et al. | |
| 9,200,508 | B2* | 12/2015 | Duncan | E21B 47/123 |
| 9,512,717 | B2* | 12/2016 | Skinner | E21B 47/123 |
| 9,739,142 | B2* | 8/2017 | Cooper | E21B 47/123 |
| 10,018,749 | B2* | 7/2018 | Cooper | G01V 11/002 |
| 2004/0065439 | A1* | 4/2004 | Tubel | E21B 23/03 166/250.15 |
| 2007/0017672 | A1* | 1/2007 | Kayadarma | E21B 47/0007 166/250.01 |
| 2008/0130412 | A1* | 6/2008 | Fink | E21B 47/16 367/82 |
| 2008/0307875 | A1* | 12/2008 | Hassan | E21B 47/091 73/152.16 |
| 2009/0188665 | A1* | 7/2009 | Tubel | E21B 23/03 166/250.01 |
| 2009/0277629 | A1* | 11/2009 | Mendez | E21B 41/0085 166/250.01 |
| 2009/0304322 | A1* | 12/2009 | Davies | G01H 9/004 385/12 |
| 2010/0038079 | A1* | 2/2010 | Greenaway | E21B 47/0007 166/254.2 |
| 2010/0191484 | A1 | 7/2010 | Schoonover | |
| 2010/0247335 | A1* | 9/2010 | Atherton | E21B 43/128 417/53 |
| 2010/0300683 | A1* | 12/2010 | Looper | E21B 21/06 166/250.01 |
| 2011/0090496 | A1* | 4/2011 | Samson | E21B 47/065 356/301 |
| 2012/0027630 | A1* | 2/2012 | Forsberg | E21B 43/128 417/423.3 |
| 2012/0046866 | A1* | 2/2012 | Meyer | E21B 28/00 702/6 |
| 2012/0067118 | A1 | 3/2012 | Hartog et al. | |
| 2012/0092960 | A1* | 4/2012 | Gaston | E21B 47/101 367/35 |
| 2012/0111104 | A1* | 5/2012 | Taverner | G01H 9/004 73/152.16 |
| 2012/0132417 | A1* | 5/2012 | Dria | E21B 47/0006 166/250.01 |
| 2012/0179378 | A1* | 7/2012 | Duncan | E21B 47/123 702/8 |
| 2012/0191633 | A1* | 7/2012 | Liu | E21B 47/0007 706/12 |
| 2014/0111348 | A1* | 4/2014 | Skinner | E21B 47/123 340/854.7 |
| 2014/0290357 | A1* | 10/2014 | Zhang | G01F 23/246 73/295 |
| 2015/0075276 | A1* | 3/2015 | Cooper | E21B 47/123 73/152.58 |
| 2015/0167661 | A1* | 6/2015 | Garvey | F04B 51/00 702/183 |
| 2016/0265905 | A1* | 9/2016 | Duncan | E21B 43/128 |
| 2016/0290126 | A1* | 10/2016 | Rendusara | E21B 47/12 |
| 2017/0107989 | A1* | 4/2017 | Coste | F04D 15/0077 |
| 2017/0108615 | A1* | 4/2017 | Cooper | G01V 11/002 |
| 2017/0122094 | A1* | 5/2017 | Chugunov | E21B 47/0007 |
| 2017/0130574 | A1* | 5/2017 | Nunes | G01V 1/226 |
| 2017/0167245 | A1* | 6/2017 | Dickenson | E21B 47/00 |

OTHER PUBLICATIONS

Examination Report for European Patent Application No. 15743078.6, dated Oct. 6, 2017, 5 pages.

* cited by examiner

MONITORING OF EQUIPMENT ASSOCIATED WITH A BOREHOLE/CONDUIT

CROSS-REFERENCE TO RELATED APPLICATIONS

This application claims the benefit of U.S. Provisional Application No. 61/934,614 titled "Pump Monitoring and Optimization Using Distributed Vibration Sensing" filed Jan. 31, 2014.

BACKGROUND

Embodiments of the present disclosure relate to monitoring systems and methods for use with equipment associated with a borehole or other conduit. In particular but not by way of limitation embodiments relate to systems and methods for monitoring vibration.

Boreholes, such as wellbores, are typically drilled for the purpose of hydrocarbon exploration or extraction, but may also be used for geothermal purposes, carbon dioxide sequestration and/or the like. Monitoring equipment may be provided in association with such boreholes to monitor one or more characteristics of the borehole, a reservoir associated with the borehole, and/or downhole equipment which has been introduced into the borehole.

Similarly, monitoring equipment may be introduced into conduits such as pipelines, pipes at the surface of a borehole and/or the like to monitor one or more characteristics of the pipeline/pipes. By way of example, a borehole may be drilled in a formation under a sea or the like, and pipes/pipelines may be associated with the borehole for providing access to the subsea borehole and/or producing hydrocarbons from the subsea borehole.

Conventional wireline tools are disruptive to the normal operation of a borehole, expensive, and cumbersome. Recently, monitoring equipment using optical fibre sensors has been developed. Such equipment can be used without disruption to normal operation of a borehole and is generally robust against the harsh operating conditions often found in boreholes.

Monitoring equipment may be used, in particular, to monitor vibrations associated with equipment such as a pump that may be used in a borehole or a pipe associated with a borehole—an example of such a pump is an Electrical Submersible Pump ("ESP").

Pumps, such as ESP, may be used to cause or enhance production from an oil producing well. The pumps may also be used to de-water a gas producing well, or pump water from an aquifer.

In general, pumps used in boreholes and/or associated pipes have a finite run time, typically of the order of two to four years. Replacement of the pumps may be expensive—particularly in an offshore environment where workover costs are potentially significant. The operational run time of a pump is likely to be reduced by exposure to high temperatures, repeated started and stopping of the pump, operation at an incorrect frequency and/or speed, high gas content in the fluid being pumped, the pumping of corrosive fluids, and/or sand in the pumped fluid. Similar issues arise in relation to other equipment which is used in relation to boreholes and other conduits.

BRIEF SUMMARY

An aspect of embodiments of the present disclosure provides a monitoring system for one or more items of equipment associated with a borehole or other conduit. The monitoring system comprises a sensor system having a vibration sensor subsystem that is configured to output sensor information indicative of vibrations at one or more sensor locations associated with one or more items of the equipment and/or locations in the borehole or other conduit. \the sensor system includes a processing system that is configured to process the sensor information to determine a characteristic of the operation of the one or more items of equipment and/or the borehole or other conduit.

The processing system may be further configured to output control information to control the operation of the one or more items of equipment based on the determined characteristic.

The control information may include an instruction to shutdown, start-up, slow down, or speed up the one or more items of equipment.

In some embodiments, the processing system may use forward modelling to predict characteristics of operation of the one or more items of equipment after its operation has been adjusted by the output control. Further sensing of characteristics of the one or more items of equipment after application of the output control may be used to provide for further adjustments to the output control and/or processing of operating characteristics of the one or more items of equipment. In some embodiments, characteristics of the one or more items of equipment may be sensed and processed when a known control output is applied to the one or more items of equipment. For example, characteristics may be sensed at a start-up/shut-down of the one or more items of equipment and the characteristics may be processed based upon knowledge of the operation/change in operation of the one or more items of equipment at the time of sensing.

The characteristic may include a frequency spectrum of the vibrations at the one or more sensor locations.

The processing system may be further configured to compare the frequency spectrum with one or more historic frequency spectra to determine a status or imminent event in relation to the one or more items of equipment.

The status or imminent event may include one or more of: a failure of the one or more items of equipment, an imminent failure of the one or more items of equipment, inefficient operation of the one or more items of equipment, and damage to part of the one or more items of equipment.

The processing system may be further configured to determine a plurality of frequency spectra, with each frequency spectrum relating to a different time period, and to analyse the plurality of frequency spectra to identify one or more changes in the frequency spectra.

The one or more changes may include a change of frequency of vibrations and/or a change of amplitude or magnitude of vibrations.

The frequency spectrum, or each spectra, may be generated using sensor information from a plurality of the one or more sensor locations which has been summed in the frequency domain.

The summation may be a weighted summation based on the position of the one or more sensor locations.

The characteristic may include one or more harmonic frequencies of vibration.

The processing system may be further configured to compare the one or more harmonic frequencies with one or more historic harmonic frequencies to determine a status or imminent event in relation to the one or more items of equipment.

The characteristic may include a liquid-gas interface location.

The characteristic may include a sand production rate.

The characteristic may be an indication of gases in fluid passing through or past the one or more items of equipment.

Determining a characteristic of the operation of the one or more items of equipment and/or the borehole or other conduit may include outputting an audio signal representative of vibrations at the one or more sensor locations.

The one or more items of equipment may include a pump and the one or more sensor locations are associated with the pump.

The pump may be an electrical submersible pump.

The vibration sensing subsystem may include one or more optical fibres and the one or more sensor locations are locations along a length of the one or more optical fibres. Where multiple fibres are used they may have different coupling to the pumping system, flow or surrounding wellbore so as to detect different phenomena. For example, a fiber loosely coupled to the equipment will be more sensitive to changes in the flow whereas a fiber coupled to the equipment will detect vibration due to the equipment.

The vibration sensor subsystem may be a distributed vibration sensor.

The distributed vibration sensor may be a heterodyne distributed vibration sensor.

The vibration sensor subsystem may include: an electromagnetic radiation source configured to emit electromagnetic radiation along the optical fibre and located at a first location; and an electromagnetic radiation receiver configured to receive electromagnetic radiation reflected towards the first location by the optical fibre or one or more other components of the vibration sensor subsystem.

The vibration sensor subsystem may be further configured to output temperature sensor information indicative of the temperature at one or more of the sensor locations.

The vibration sensor subsystem may include at least one Bragg grating at one or more of the sensor locations. These may be evenly distributed along the length of the pumping system or specifically aligned with elements of the pumping system.

In some embodiments, the vibration sensor may include defects, non-linearities or the like that may be used to create reference/baseline outputs. The defects, non-linearities or the like may be disposed/created at known location along the conduit.

The processing system may be further configured to output control information to control the operation of the one or more items of equipment and the vibration sensor subsystem may be further configured to output sensor information indicative of vibrations at one or more sensor locations caused as the result of the operation of the one or more items of equipment in accordance with the control information.

The monitoring system may further comprise an auxiliary sensor subsystem which is configured to output auxiliary sensor information to the processing system, the auxiliary sensor information being indicative of an aspect of the operation of the one or more items of equipment, wherein the processing system may be further configured to determine the characteristic based on the sensor information and the auxiliary sensor information.

The characteristic of the one or more items of equipment and/or the borehole or other conduit may include a flow condition for fluid upstream or downstream of the one or more items of equipment.

An aspect provides a method of monitoring one or more items of equipment associated with a borehole or other conduit, the method comprising: outputting sensor information indicative of vibrations at one or more sensor locations, the one or more sensor locations being associated with one or more items of the equipment and/or the borehole or other conduit; and processing the sensor information to determine a characteristic of the operation of the one or more items of equipment and/or the borehole or other conduit.

The method may further comprise: outputting control information to control the operation of the one or more items of equipment based on the determined characteristic.

The control information may include an instruction to shutdown, start-up, slowing down, or speeding up the one or more items of equipment.

The characteristic may include a frequency spectrum of the vibrations at the one or more sensor locations.

The method may further comprise: comparing the frequency spectrum with one or more historic frequency spectra to determine a status or imminent event in relation to the one or more items of equipment.

The status or imminent event may include one or more of: a failure of the one or more items of equipment, an imminent failure of the one or more items of equipment, inefficient operation of the one or more items of equipment, and damage to part of the one or more items of equipment.

The method may further comprise: determining a plurality of frequency spectra, with each frequency spectrum relating to a different time period; and analysing the plurality of frequency spectra to identify one or more changes in the frequency spectra.

The one or more changes may include a change of frequency of vibrations and/or a change of amplitude or magnitude of vibrations.

The method may further comprise: generating the frequency spectrum, or each spectra, using sensor information from a plurality of the one or more sensor locations which has been summed in the frequency domain.

The summation may be a weighted summation based on the position of the one or more sensor locations.

The characteristic may include one or more harmonic frequencies of vibration.

The method may further comprise: comparing the one or more harmonic frequencies with one or more historic harmonic frequencies to determine a status or imminent event in relation to the one or more items of equipment.

The characteristic may include a liquid-gas interface location.

The characteristic may include a sand production rate.

The characteristic may be an indication of gases in fluid passing through or past the one or more items of equipment.

Processing the sensor information to determine a characteristic of the operation of the one or more items of equipment and/or the borehole or other conduit may include outputting an audio signal representative of vibrations at the one or more sensor locations.

The one or more items of equipment may include a pump and the one or more sensor locations are associated with the pump.

The pump may be an electrical submersible pump.

The one or more sensor locations may be locations along a length of one or more optical fibres.

The vibration sensor subsystem may be a distributed vibration sensor.

The distributed vibration sensor may be a heterodyne distributed vibration sensor.

The method may further comprise: emitting electromagnetic radiation along an optical fibre from a first location; and receiving electromagnetic radiation reflected towards the first location by the optical fibre or one or more other components of a vibration sensor subsystem.

The method may further comprise: outputting temperature sensor information indicative of the temperature at one or more of the sensor locations.

The method may further comprise: outputting control information to control the operation of the one or more items of equipment; and outputting sensor information indicative of vibrations at one or more sensor locations caused as the result of the operation of the one or more items of equipment in accordance with the control information.

The method may further comprise: outputting auxiliary sensor information indicative of an aspect of the operation of the one or more items of equipment, and determining the characteristic includes determining the characteristic based on the sensor information and the auxiliary sensor information.

The characteristic of the one or more items of equipment and/or the borehole or other conduit may include a flow condition for fluid upstream or downstream of the one or more items of equipment.

Another aspect may comprise a combination of an item of equipment and an optical fibre, the combination being associated with a borehole or other conduit, wherein: the optical fibre is wrapped around at least part of the item of equipment, and the optical fibre includes one or more elements along its length which are each configured to reflect at least part of electromagnetic radiation directed along the optical fibre, such that the optical fibre is useable in a distributed vibration sensor and/or a distributed temperature sensor.

The optical fibre may be wrapped in a spiral configuration around at least part of the item of equipment.

BRIEF DESCRIPTION OF THE DRAWINGS

The present disclosure is described in conjunction with the appended figures. It is emphasized that, in accordance with the standard practice in the industry, various features are not drawn to scale. In fact, the dimensions of the various features may be arbitrarily increased or reduced for clarity of discussion.

Figure 1:
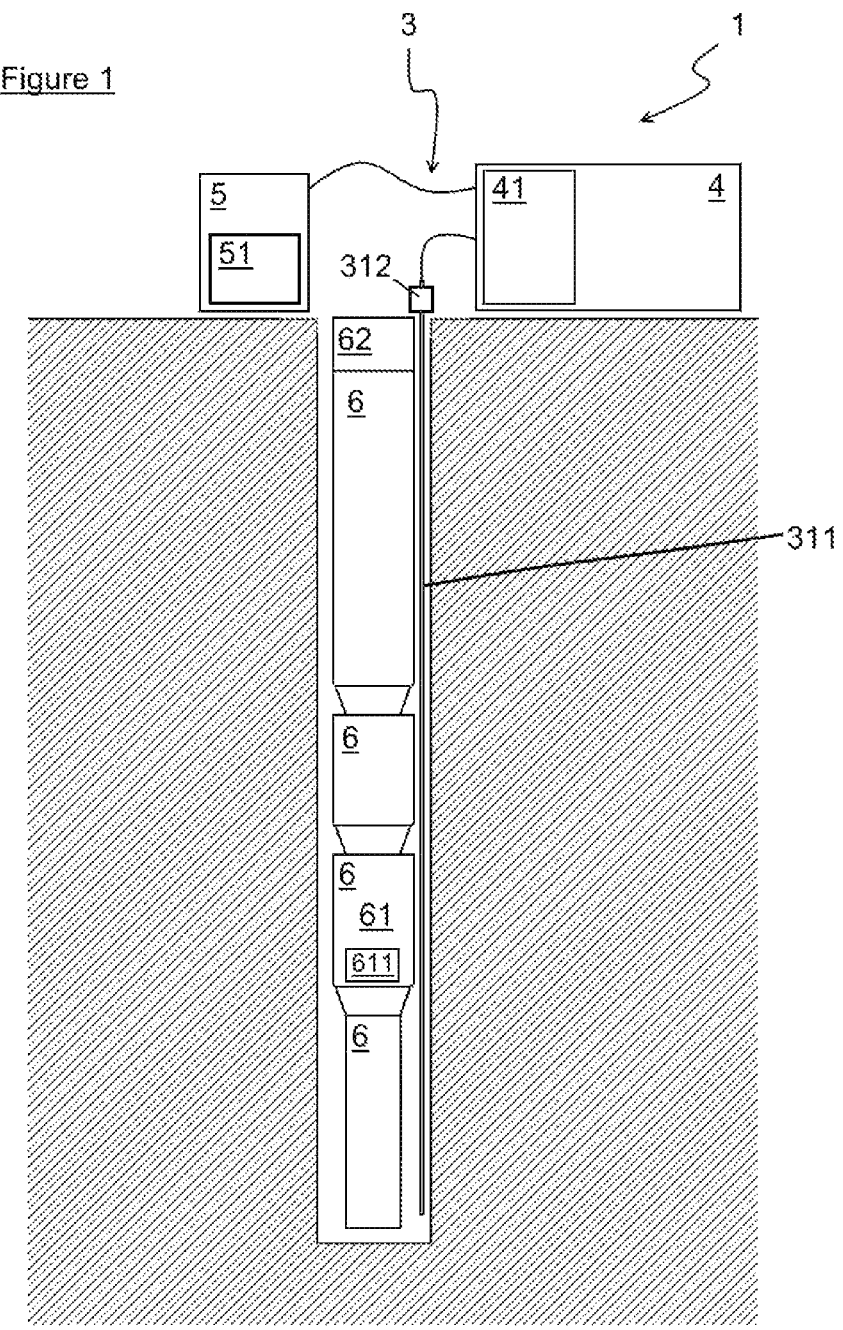
FIG. 1 shows a schematic view of a monitoring system and other components in accordance with some embodiments.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

With reference to FIG. 1, embodiments of the present disclosure are configured for use in relation to equipment 6 associated with a borehole or other conduit 2 which may be used for hydrocarbon exploration or extraction, or carbon dioxide sequestration. The borehole or other conduit 2 may, therefore, be a wellbore associated with a hydrocarbon well and a hydrocarbon reservoir.

The equipment 6 may include a plurality of items of equipment 6 which are used to create, operate, or maintain the borehole or other conduit 2.

This equipment 6 may include a pump 61 and the pump 61 may be an Electrical Submersible Pump ("ESP").

The pump 61 may be configured to pump (or otherwise drive movement of) a fluid through at least part of the borehole or other conduit 2, for example. In some example embodiments, the fluid may be a hydrocarbon or water. The pump 61 may be configured to lift the fluid through at least part of the borehole or other conduit 2 and this may include, for example, moving the fluid up the borehole or other conduit 2 and/or out of the borehole or other conduit 2. Thus, in some examples, the pump 61 may be configured to assist in the movement of fluids from a fluid reservoir which may be an underground reservoir. In some specific examples, the pump 61 may be configured to pump a hydrocarbon fluid from an underground reservoir through at least part of the borehole or other conduit 2, and/or the pump 61 may be configured to pump water from the borehole or other conduit 2 prior to the passage of a hydrocarbon fluid through the borehole or other conduit 2.

Figure 8:
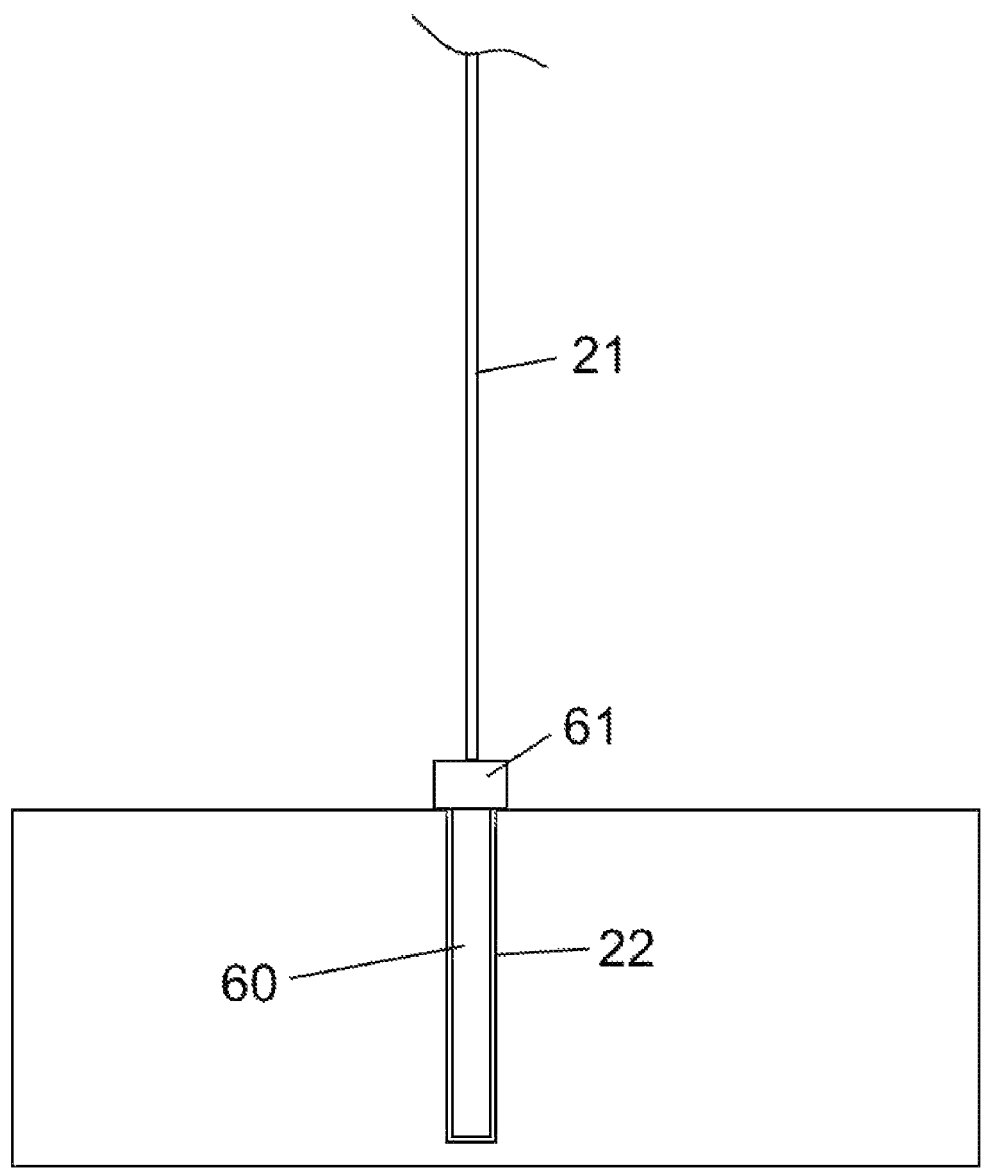
FIG. 8 shows a conduit and borehole according to some embodiments.

In some embodiments, the pump 61 is a booster pump which is configured to boost the flow of fluid through the borehole or other conduit 2. For example, with reference to FIG. 8, the pump 61 may be associated with a conduit 21 which is configured to receive the fluid from a borehole 22 and through which the fluid may be transported to another location (such as from a subsea borehole 22 to a rig or ship at the surface of the sea or a land-based installation). In such embodiments, the pump 61 may or may not be located within the conduit 21. For example, the pump 61 could be located near or on a seafloor.

As will be understood, therefore, in some embodiments, the pump 61 may be part of downhole equipment associated with the borehole 22 and the downhole equipment may be configured to be received within the borehole 22. In some embodiments, however, the pump 61 is associated with the borehole 22 but may be configured to be located outside of the borehole (e.g. adjacent or proximal thereto). Similarly, the pump 61 may be part of equipment which is configured to be received by the conduit 21 or may be part of equipment which is configured to be located outside of the conduit 21.

The pump 61 may be part of a pumping system which includes one or more other pumps (which may be part of the downhole equipment or otherwise associated with the borehole or other conduit 2).

In some embodiments, one or more items of the equipment 6 (such as the pump 61) may be driven by a Variable Speed Drive ("VSD") 62. The Variable Speed Drive 62 is configured to drive the one or more items of the equipment 6 (e.g. the pump 61) at a plurality of different drive frequencies. The Variable Speed Drive 62 may, itself, be part of the equipment 6.

Figure 2:
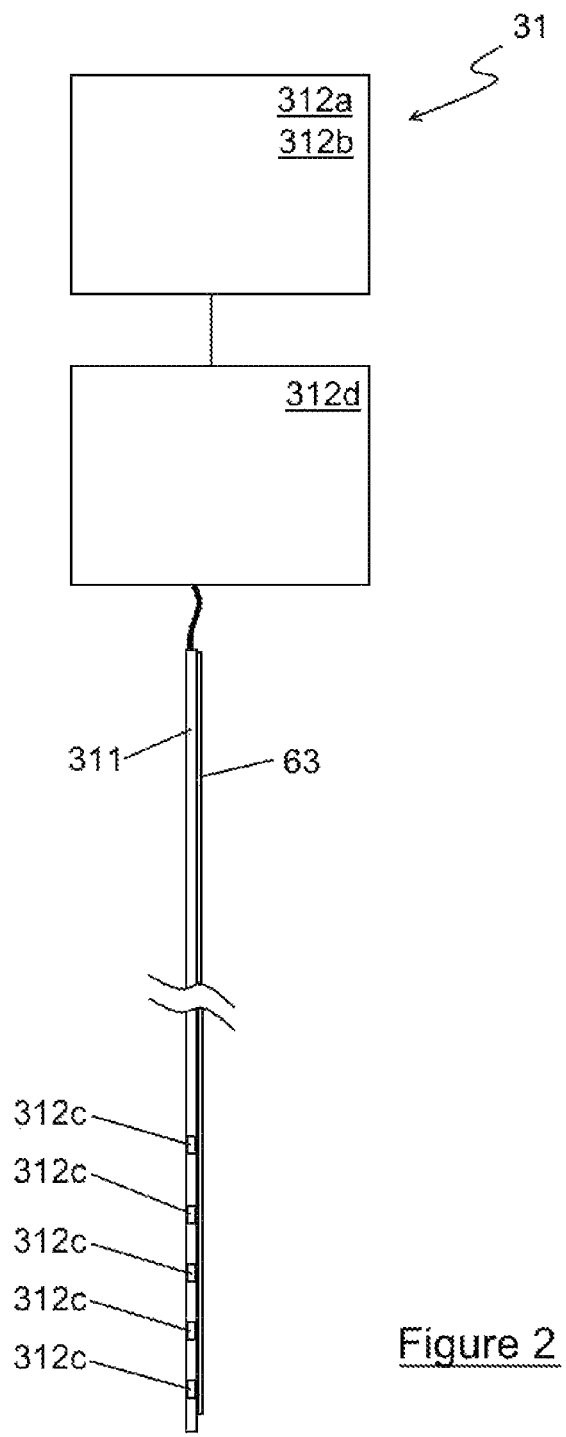
FIG. 2 shows a vibration sensor subsystem in accordance with some embodiments.
Figure 3:
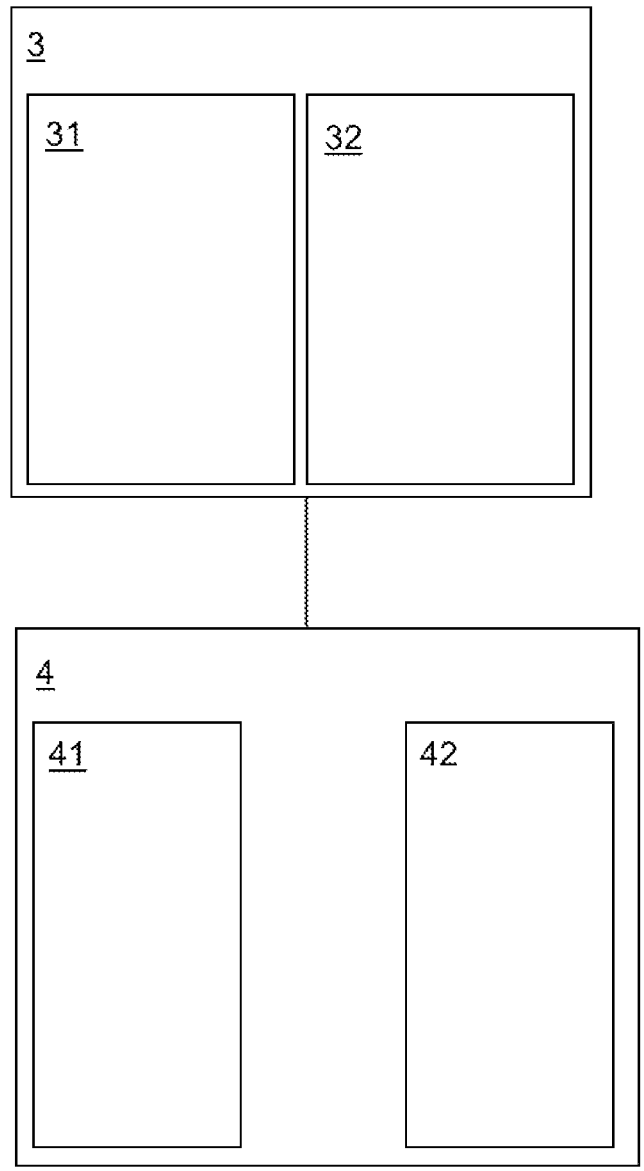
FIG. 3 shows a sensor system and a processing system in accordance with some embodiments.

With further reference to FIGS. 1 to 3, some embodiments of the present disclosure include a monitoring system 1 for use in relation to the borehole or other conduit 2 and/or the equipment 6.

The monitoring system 1 includes a sensor system 3 and a processing system 4 which is communicatively coupled to the sensor system 3.

The sensor system 3 is configured to output sensor information to the processing system 4 which is, in turn, configured to receive the sensor information from the sensor system 3. The processing system 4 is further configured to process the sensor information. This may result in the processing system 4 determining one or more parameters indicative of an aspect of the borehole or other conduit 2 and/or equipment 6 associated with the borehole or other conduit 2. For example, the processing system 4 may be configured to determine a parameter which is indicative of the flow of fluid through the borehole or other conduit 2 and/or through the equipment 6 associated with the borehole or other conduit 2. Alternatively, or in addition, the processing system 4 may be configured to determine a parameter which is indicative of the condition of the equipment 6, and/or the borehole or other conduit 2. In some examples, the processing system 4 is configured to process the sensor information by collating the sensor information, identifying trends in the sensor information, and/or identifying changes in sensor information.

The processing system 4 may be further configured to control the operation of the sensor system 3 such that the required sensor information is provided to the processing system 4.

Some embodiments may further include a control system 5. The control system 5 is configured to control one or more aspects of the operation of the equipment 6 (e.g. the pump 61) associated with the borehole or other conduit 2.

In some embodiments, the monitoring system 1 (and, in particular, the processing system 4) and the control system 5 are communicatively coupled. In such embodiments, the control system 5 may be configured to control the operation of at least one of the one or more aspects of the operation of the equipment 6 (e.g. the pump 61) based at least in part on control information received at the control system 5 from the monitoring system 1. The control information may be generated by the processing system 4 and may be based on the one or more parameters determined by the processing system 4.

The sensor system 3 of the monitoring system 1 includes a vibration sensor subsystem 31. The vibration sensor subsystem 31 is configured to determine the sensor information, wherein the sensor information is indicative of (or otherwise represents) vibrations associated with one or more parts of the vibration sensor subsystem 31—e.g. at a rate of several kHz. The locations of these parts of the vibration sensor subsystem 31 are generally referred to as "sensor locations". These parts of the vibration sensor subsystem 31 (i.e. the sensor locations) may be located at, on, or adjacent parts of the borehole or other conduit 2, or parts of the equipment 6 (such as the pump 61) to allow monitoring of vibrations associated therewith. Accordingly, the vibration sensor subsystem 31 is deployable in relation to the borehole or other conduit 2 and, in particular, may be securable to the equipment 6 (or a part thereof) and/or to the borehole or other conduit 2 (or a part thereof).

Accordingly, in embodiments including a pump 61, one or more of the sensor locations of the vibration sensor subsystem 31 may be located such that the sensor information which is determined in relation to those one or more sensor locations is indicative of vibrations associated with the pump 61. This sensor information may be indicative of vibrations caused by (or at least partially caused by) the pump 61 and/or indicative of vibrations to which the pump 61 is exposed or which are induced in the pump 61. Equally, in other embodiments, the one or more sensor locations of the vibration sensor subsystem 31 could be associated with another item of the equipment 6 (other than the pump 61) and the sensor information determined in relation to those one or more sensor locations may be indicative of vibrations associated with that item of the equipment 6 (i.e. caused by the item of the equipment 6 or to which the item of the equipment 6 is exposed).

The vibration sensor subsystem 31 may be configured to determine such sensor information in relation to a plurality of items of the equipment 6 and these items may include more than one such pump 61. In addition, first and second sensor locations may be associated with one item of the equipment (e.g. the pump 61) such that first sensor information is determined indicative of vibrations at the first sensor location and second sensor information is determined indicative of vibrations at the second sensor location—the first and second sensor information relating to the same item of equipment 6 (e.g. the pump 61). The first and second sensor locations may be on either side of the item of the equipment 6 (e.g. the pump 61). This may enable, for example, sensor information indicative of vibrations associated with different parts of the same item of equipment 6 (e.g. the pump 61) to be determined (e.g. an inlet and an outlet of the pump 61). For example, in some embodiments, the sensor locations may be upstream and/or downstream of the item of equipment (e.g. the pump 61) relative to the direction of flow of fluid through the item of the equipment 6 (e.g. the pump 61). One or more further sensor locations may be associated with the same item of the equipment 6 (e.g. the pump 61).

In some embodiments, the equipment 6 includes a plurality of pumps 61 and the sensor locations may be upstream and/or downstream of and/or adjacent each pump 61 of the plurality of pumps 61.

As will be appreciated, therefore, sensor locations may be adjacent an item of the equipment 6 (e.g. the pump 61) about which sensor information is to be gathered, and/or may be upstream of the item of the equipment 6 (e.g. the pump) and/or may be downstream of the item of the equipment 6 (e.g. the pump), and/or may be at or adjacent an inlet of the item of the equipment 6 (e.g. the pump 61), and/or may be at or adjacent an outlet of the item of the equipment 6 (e.g. the pump 61).

The sensor system 3, and in particular the vibration sensor subsystem 31, may be configured to output the sensor information in relation to a plurality of sensor locations in accordance with a predetermined sequence and/or in accordance with one or more instructions received from the processing system 4.

The vibration sensor subsystem 31 may be configured to determine sensor information during operation of the equipment 6 (e.g. the pump 61) and/or during downtime, when the equipment 6 (e.g. the pump 61) is not in operation.

In some embodiments the vibration sensor subsystem 31 includes one or more optical fibres 311 and the sensor locations may each be a point along one of the one or more optical fibres 311.

The vibration sensor subsystem 31 may be a Distributed Vibration Sensing subsystem ("DVS"), which is also known as a Distributed Acoustic Sensing subsystem ("DAS"). In some embodiments, the vibration sensor subsystem 31 may be, more specifically, a heterodyne Distributed Vibration Sensing subsystem ("hDVS"). In some embodiments, the vibration sensor subsystem 31 may be a form of Distributed Vibration Sensing subsystem which is not a heterodyne Distributed Vibration Sensing subsystem. Embodiments of the present disclosure may use coherent Rayleigh backscatter, Raman backscatter, or Brillouin backscatter, or another suitable type of backscatter in the Distributed Vibration Sensor subsystem.

The vibration sensor subsystem 31 may, therefore, include one or more optical fibres 311 (which may be single mode or multimode or a mixture of both) and other components 312. The other components 312 may include an electromagnetic radiation source 312*a* which is configured to direct (i.e. transmit or emit) electromagnetic radiation along the one or more optical fibres 311 and an electromagnetic radiation receiver 312*b* which is configured to receive electromagnetic radiation from the one or more optical fibres 311. The electromagnetic radiation source 312*a* and electromagnetic radiation receiver 312*b* may be associated with a first end of the one or more optical fibres 311 (or a first location) such that the electromagnetic radiation receiver 312*b* is configured to receive electromagnetic radiation which has been reflected back towards the electromagnetic radiation source 312*a* (i.e. towards the first end or location). The or each optical fibre 311 may be one or more kilometers long. The vibration sensor subsystem 31 may be configured to determine sensor information at a plurality of locations along a length of the one or more optical fibres 311—e.g. at a rate of several kHz. Embodiments of the present disclosure may use a phase difference between the transmitted and received electromagnetic radiation to determine an indication of the strain on the one or more optical fibres 311 at the or each sensor location (which is representative of the vibration at the or each sensor location).

Figure 4:
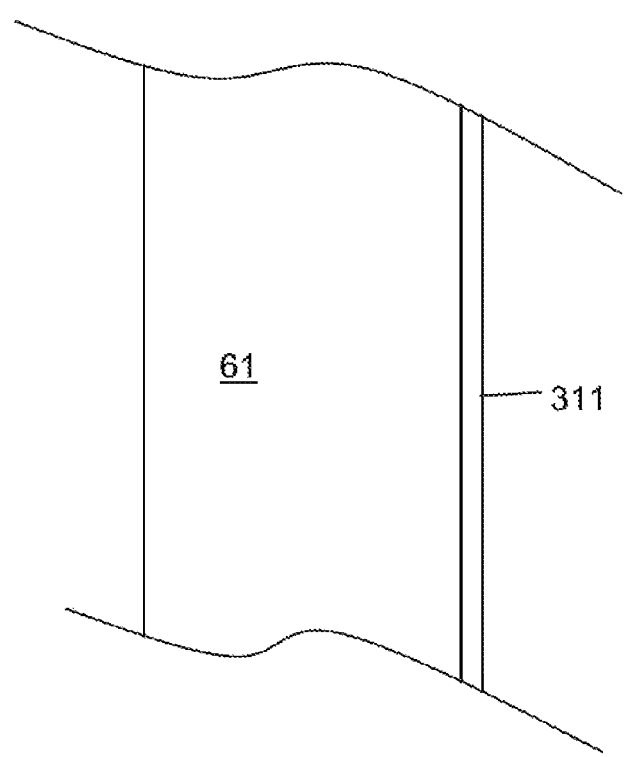
FIG. 4 shows part of a pump and optical fibre in accordance with some embodiments.

In FIG. 1, an optical fibre 311 is depicted spaced apart from the equipment 6. This, it will be appreciated is for schematic purposes. The optical fibre 311 may be secured to or in, for example, one or more of the items of the equipment 6 (e.g. the pump 61 as shown in FIG. 4).

Examples of such arrangements are described in U.S. Pat. Nos. 7,668,411, 8,347,958, 8,225,867, US2012/0067118, US2012/0179378 and U.S. Pat. No. 7,946,341 which are all incorporated by reference for all purposes. Embodiments of the present disclosure may use similar such arrangements as the vibration sensor subsystem 31.

In some embodiments, sensor locations may be substantially continuously located along a length of the vibration sensor subsystem 31 (e.g. along a length of the one or more optical fibres 311 if provided). In some embodiments, the sensor locations are determined by the location of an element 312*c* (which may be another component 312) of the vibration sensor subsystem 31 at each sensor location. This element 312*c* may be configured to reflect at least a portion of the electromagnetic radiation emitted by the electromagnetic radiation source 312*a* back towards the electromagnetic radiation source 312*a* and, hence, towards the electromagnetic radiation receiver 312*b*. The element 312*c* may be a Bragg grating, for example.

The use of an element 312*c* at each sensor location may improve the spatial resolution of the sensor information compared to reliance on intrinsic scattering of the electromagnetic radiation in the one or more optical fibres 311. For example, spatial resolution may be improved from about 5 m without the use of the elements 312*c* to about 10 cm or less using the elements 312*c* in accordance with some embodiments of the disclosure.

The elements 312*c* may be used in a conventional manner to determine temperature information at the sensor locations (which may also, therefore, be temperature sensor locations).

In some embodiments, one or more switches or filters 312*d* are associated with the one or more optical fibres 311 and/or the electromagnetic radiation receiver 312*b* and/or the electromagnetic radiation source 312*a*. The one or more switches or filters 312*d* are configured to modulate the operation of the vibration sensor subsystem 31 such that both temperature information and sensor information (indicative of vibration) can be obtained from the same one or more optical fibres 311. This modulation may be achieved by modulating over time (e.g. using a switch of the one or more switches or filters 312*d*) or operating at two wavelengths (one for determining the temperature information and one for determining the sensor information (indicative of vibration)) and filtering using a filter of the one or more switches or filters 312*d*.

In some embodiments in which the vibration sensor subsystem 31 includes one or more optical fibres 311, the one or more optical fibres 311 include at least one optical fibre 311 which extends along an electrical power transmission cable 63. The electrical power transmission cable 63 may be a cable providing electrical power to the one or more items of the equipment 6 (e.g. the pump 61). The optical fibre 311 may be provided in or coupled to a conduit (e.g. a pipe), or a cord for the electrical power transmission cable 63.

The optical fibre 311 along the electrical power transmission cable 63 may be used to monitor the temperature at one or more temperature sensor locations along the length of the cable 63—this may include the use of the elements 312*c*. Thus, the sensor system 3 may be configured to output temperature information. The optical fibre 311 may be further used to generate sensor information (indicative of vibration) associated with sensor locations along with the length of the cable 63.

In some embodiments, a plurality of substantially parallel optical fibres 311 may be provided for redundancy. In some embodiments, a plurality of substantially parallel optical fibres 311 is provided wherein each of the optical fibres 311 has different coupling characteristics to the surrounding environment such that different sensor information may be obtained from each of the plurality of substantially parallel optical fibres for substantially the same sensor locations. For example, a first optical fibre 311 may be closely coupled to one or more of the items of equipment 6 (e.g. the pump 61). A second optical fibre 311 may be located in a fluid flow path through the one or more of the items of equipment 6 (e.g. the pump 6) such that the fibre 311 may vibrate in the fluid flow.

The sensor information may include a combination of sensor information from such optical fibres 311.

In some embodiments, one or more of the optical fibres 311 is wrapped around one or more of the items of the equipment 6 (e.g. the pump 61) in a spiral or other configuration. Similarly, one or more of the optical fibres 311 may be wrapped around one or more cables (such as the electrical power transmission cable 63), or control lines, in a spiral or other configuration. The wrapping of one or more of the optical fibres 311 in such a spiral or other configuration may increase the length of optical fibre for a given length of item of the equipment 6, or borehole or other conduit 2. In some embodiments, for example, 50 m or more of optical fibre 311 may be coupled to an item of the equipment 6 (such as the pump 61) over a length of less than 5 m. In some embodiments, for example, 100 m or more of optical fibre 311 may be coupled to an item of the equipment 6 (such as the pump 61) over a length of less than 5 m. This may increase the spatial resolution of the sensor information.

It has been found that it is possible to separate out data and/or process characteristics of a device/a location in a conduit from multiple measurements from separate fibres coupled to and/or disposed at the device/location.

Embodiments of the present disclosure include methods and mechanisms for deploying one or more optical fibres 311 for use with other embodiments.

In accordance with a first optical fibre deployment method, after installation of the completion for a borehole 21, a control line may be strapped or otherwise attached to the production tubing and the optical fibre may be pumped through after installation of the production tubing.

In accordance with a second optical fibre deployment method, a cable containing one or more optical fibres may be strapped or otherwise attached to the production tubing.

In accordance with a third optical fibre deployment method, a cable or control line containing one or more optical fibres may be strapped or otherwise attached to a tail pipe which may hang below the pump 61 (thus allowing deployment below the pump 61).

In accordance with a fourth optical fibre deployment method, the optical fibre 311 may be left loose in the borehole or other conduit 2 below the pump 61 (to achieve deployment below the pump 61).

The one or more optical fibres 311 discussed herein may, for example, be attached to tubing of the borehole or other conduit 2 or may be cemented behind it, for example.

In some embodiments, the sensor system 3 includes an auxiliary sensor subsystem 32. The auxiliary sensor subsystem 32 may be configured to monitor one or more aspects of the operation of one or more items of the equipment 6, and/or the borehole or other conduit 2. The auxiliary sensor subsystem 32 is further configured to provide auxiliary sensor information to the processing system 4, the auxiliary sensor information representing one or more monitored aspects.

For example, auxiliary sensor subsystem 32 may be configured to monitor one or more of: the flow rate of fluid through the borehole or other conduit 2 at one or more locations, the flow rate of fluid through or past one or more items of the equipment 6, the fluid pressure at one or more locations within the borehole or other conduit 2, the fluid pressure in one or more items of the equipment 6, the electric current drawn by a motor of one of the items of equipment 6, the voltage of electricity supplied to a motor of one of the items of equipment 6, the temperature of one or more items of the equipment 6, the temperature of a motor of one of the items of equipment 6, the temperature of the fluid in the borehole or other conduit 2, the temperature of the fluid in one or more items of the equipment 6, and/or the movement or acceleration of one or more parts of the one or more items of the equipment 6 (e.g. measures by accelerometers).

The auxiliary sensor subsystem 32 could be wholly or partially realised as a subsystem of the control system 5 in some embodiments and may not be part of the sensor system 3.

In embodiments in which the monitoring system 1 and the control system 5 are communicatively coupled, the processing system 4 of the monitoring system 1 may be communicatively coupled to the control system 5.

In some embodiments, the control system 5 may be configured (e.g. in response to an instruction from the processing system 4) to control the operation of one or more items of the equipment 6 (such as the pump 61) associated with the borehole or other conduit 2 in a manner which is intended to produce a predetermined vibration signature.

In some embodiments, the control system 5 may be configured (e.g. in response to an instruction from the processing system 4) to control the operation of one or more items of the equipment 6 (such as the pump 61) in accordance with a predetermined sequence of commands. These commands may include one or more commands to start up, shutdown, speed up, and slow down.

The resulting sensor information indicative of vibrations which are generated in association with one or more items of the equipment 6 (such as the pump 61) may be determined by the sensor system 3 and, in particular, by the vibration sensor subsystem 31.

The sensor information which is consequently determined by the sensor system 3 may then be passed to the processing system 4 for processing.

The controlling of the one or more items of equipment 6 in a predetermined manner (e.g. in accordance with a predetermined sequence of commands or to generate a predetermined vibration signature) to determine resulting sensor information may be considered to be "active sensing". In contrast, "passive sensing" may refer to the determining of sensor information during normal operation of the one or more items of the equipment 6 (i.e. during operation of the one or more items which was not primarily intended to allow the sensor information to be determined).

Although embodiments are described such that the processing system 4 provides one or more instructions to the control system 5, equally, the processing system 4 may output a parameter to the control system 5 which the control system 5 then analyses to determine how to control one or more items of the equipment 6—e.g. to optimise the operation of the one or more items of the equipment 6 (which may include the pump 61 or which may include a plurality of pumps).

As discussed above, the processing system 4 is configured to receive the sensor information from the sensor system 3 and this information is indicative of vibrations detected at the sensor location to which the sensor information relates.

The processing system 4 may receive sensor information relating to one or more sensor locations and may periodically receive new sensor information for those one or more sensor locations. As discussed above, the processing system 4 may also be configured to instruct the operation of the sensor system 3 such that required sensor information is provided to the processing system 4.

The processing system 4 may store sensor information in an archive 41 of the processing system 4 for later use. The processing system 4 may also or alternatively perform one or more calculations using the sensor information to determine one or more parameters associated with the borehole or other conduit 2 and/or associated with the equipment 6.

Example operations of the processing system 4 are described below. As will be appreciated, the same processing system 4 may perform one or more of these processes.

Figure 5:
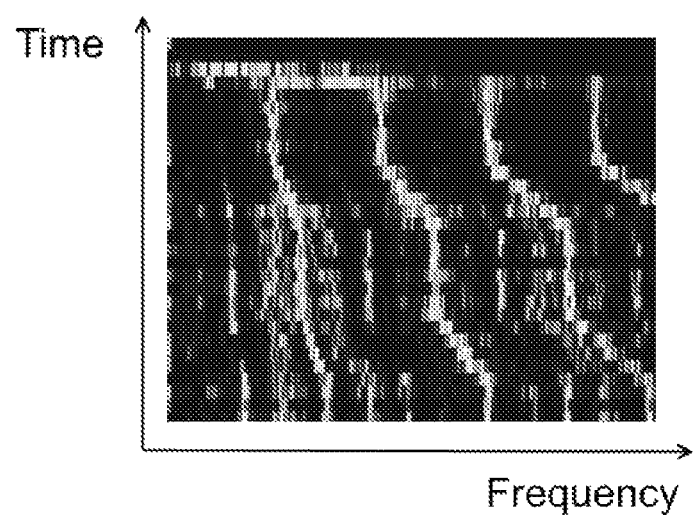
FIG. 5 shows a graphical representation of frequency spectra according to some embodiments.

In embodiments, the processing system 4 is configured to generate vibration frequency trend information associated with an item of the equipment 6 (e.g. the pump 61). This may be achieved by generating frequency spectra for vibrations associated with the item of the equipment 6 (e.g. the pump 61). The frequency spectra may be presented graphically and/or may be further processed by the processing system 4 without graphical representation in order to identify trend information. An example graphical representation of frequency spectra generated by the processing system 4 in relation to sensing information associated with a pump 61 is shown in FIG. 5.

The frequency spectra may be determined by intermittently collecting sensor information from one or more sensor locations associated with the item of equipment 6 (e.g. the pump 61). Frequency and amplitude (or magnitude) information may be extracted from the sensor information at each intermittent collection time to provide a frequency spectrum for that collection time (this may be plotted for a graphical representation with different colours for different vibration magnitudes/amplitudes). If sensor information from a plurality of sensor locations is collected then it may be summed and that summation may be weighted (as described herein). This process may be repeated (with each frequency spectrum being plotted adjacent the preceding frequency spectrum to build the frequency spectra).

Trends and changes in the frequency spectra generated from the sensor information may then be determined.

The frequency spectra are obtained intermittently at a predetermined interval. This interval may be once every second, minute, hour, etc. The frequency spectra may each be obtained over a monitoring period which may be a second, a minute, five minutes, etc. Thus, a frequency spectrum may represent the sum of the frequencies of vibration observed at one or more sensor locations over the monitoring period and a new frequency spectrum may be obtained every predetermined interval.

Examples of frequency spectra may be stored in the archive 41 (or elsewhere) representing known events such as:
a. the failure or onset of failure or likely imminent failure of an item of the equipment 6 (e.g. pump 61 failure); and/or
b. the failure or onset of failure or likely imminent failure of a component of an item of the equipment 6 (e.g. a component of the pump 61); and/or
c. inefficient operation of an item of the equipment 6 (e.g. the pump 61); and/or
d. changes in one or more properties of the fluid passing by or through an item of the equipment 6 (e.g. the pump 61); and/or
e. the onset of gas locking event; and/or
f. cavitation in the pump 61 which may result in damage to the pump 61; and/or
g. the onset of damage to the pump 61 as a result of cavitation.

The processing system 4 may be configured to compare a current frequency spectra (i.e. associated with current operation of an item of equipment 6 such as a pump 61) with a stored example. The processing system 4 may be configured to determine a likely status or imminent event in relation to the item of equipment 6 (e.g. the pump 61) based on a similarity between a stored example frequency spectra and the current frequency spectra.

In some embodiments, the processing system 4 includes a display 42 and the processing system 4 is configured to display a graphical representation of the current frequency spectra. The processing system 4 may be further configured to display (e.g. adjacent or as an overlay) one or more of the stored example frequency spectra so that an operator can compare the spectra and determine a likely status or imminent event in relation to the item of equipment 6 (e.g. the pump 61). The processing system 4 may be configured to receive an input from the operator indicating a status or imminent event in relation to the item of equipment 6 (e.g. the pump 61).

In some embodiments, the processing system 4 is configured to identify one or more changes in the frequency spectra which are likely to be indicative of a status or imminent event in relation to the item of the equipment 6 (e.g. the pump 61). For example, the appearance or disappearance of peaks in one or more of the frequency spectra may indicate the item of the equipment 6 (e.g. the pump 61) or a component thereof is starting to fail, is likely to fail, is failing, or has failed.

In some embodiments, modelling is used to generate one or more stored example frequency spectra and/or to identify one or more changes which are likely to be indicative of a status or imminent event in relation to the item of the equipment 6 (e.g. the pump 61) or a component thereof.

A status or imminent event may include failure, failing, likely failure, inefficient operation, a change in fluid properties (for the fluid passing though the item of the equipment 6 (e.g. being pumped by the pump 61)). The status or imminent event may include a gas locking event.

In accordance with some embodiments, the processing system 4 may be configured to send control information to the control system 5 as a result of the processing system 4 determining a status or imminent event in relation to the item of equipment 6 (e.g. the pump 61) and/or receiving an input from the operator indicating a status or imminent event in relation to the item of equipment 6 (e.g. the pump 61). The control information may instruct a change in the operation of an item of the equipment 6 (which may or may not be the same item of the equipment 6 about which the sensor information related).

The change in the operation of the item of the equipment 6 may include the slowing down, speeding up, shutting down, or starting up of the item. This may assist in reducing the number of occasions in which the item of the equipment 6 must be started or shutdown—which can be beneficial for increasing the lifetime of many items of the equipment 6 (e.g. the pump 61).

In some embodiments, the processing system 4 may be configured to schedule maintenance automatically as a result of the determined status or imminent event. In some embodiments, the processing system 4 may be configured to prompt the operator automatically to schedule maintenance as a result of the determined status or imminent event. Scheduling maintenance may include the ordering of a replacement item of the equipment 6 (e.g. the pump 61) and/or a component thereof.

Thus, embodiments seek to determine or allow the easier determination of a status or imminent event more quickly and/or easily. This may reduce downtime and allow for preplanning of maintenance work (e.g. workovers).

Although described above in relation to frequency spectra, it will be appreciated that other forms of vibration frequency trend information may be utilised.

In some embodiments, the processing system 4 is configured to assess changes in harmonic frequencies or in the amplitude/magnitude of vibrations at harmonic frequencies to determine a status or imminent event in relation to the one or more items of the equipment 6 (e.g. the pump 61). This may include comparing harmonic frequencies identified in current sensor information (e.g. from a frequency spectrum thereof) with historic harmonic frequencies stored in the archive 41 to identify one or more changes in the harmonic frequencies and/or the amplitude/magnitude of vibrations at those harmonic frequencies. Changes which are indicative of a status or imminent event may be identified by the processing system 5, which consequently performs one or more of the actions described above (such as outputting control information and/or scheduling maintenance).

Such embodiments may be implemented in relation to an item of the equipment 6 or in relation to a plurality of such items.

In embodiments which include a Variable Speed Drive 62, the harmonic frequencies may be integer or non-integer multiples of the drive frequency. The processing system 4 may be configured to identify the harmonic frequencies in the sensor information (e.g. in a frequency spectrum) by searching frequency windows around integer or non-integer multiples of the drive frequency.

In some embodiments, the blade pass frequency for a pump 61 may be substantially equal to the drive frequency multiplied by the number of pump blades. This frequency and/or the amplitude/magnitude of the vibrations at this frequency may change over time due to wear, damage or misalignment and the changes may be identified by the processing system 4 from the sensor information (e.g. from a frequency spectrum) and used to identify a status or imminent event in relation to the pump 61.

In some embodiments in which the drive frequency of the Variable Speed Drive 62 is unknown or needs to be confirmed, this may be determined by the processing system 4 which may be configured to identify likely peaks in a frequency spectrum of the sensor information which may represent the drive frequency or a harmonic thereof. In some embodiments, the drive frequency is determined by measuring the current drawn by a motor of the item or the equipment 6 (e.g. the pump 61). This may be confirmed by the processing system 4 using the above techniques.

Figure 6:
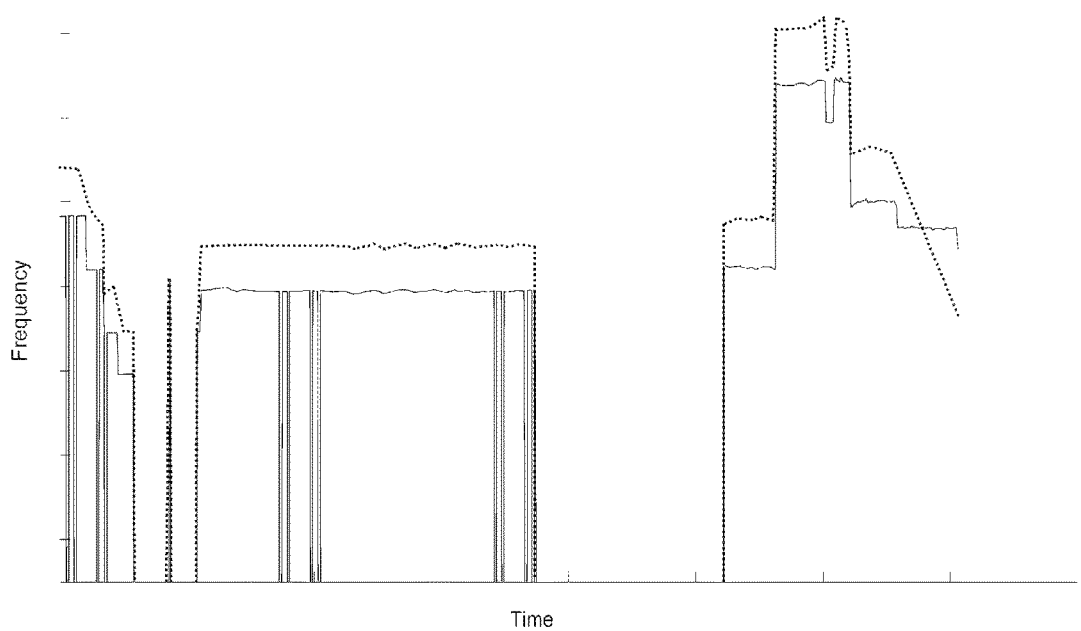
FIG. 6 shows a graph of pump frequency and drive frequency in accordance with some embodiments.

In accordance with some embodiments, the processing system 4 may be configured to compare the drive frequency of the Variable Speed Drive 62 with the operating point of the pump 61 (or other item of the equipment 6 driven by the Variable Speed Drive 62). The drive frequency and/or the operating point of the pump 61 (i.e. the actual rotational speed of a part of the pump 61 or "pump frequency") may be determined using the processes described herein. The comparison may allow the processing system 4 of some embodiments to determine motor slip in relation to a motor of the pump 61. This information may be used by the processing system 4 to output control information to the control system 5 (e.g. to seek to achieve an optimal slip characteristic). In some embodiments, that control information is a parameter indicative of the slip which is then used as feedback by a control algorithm associated with the motor and used by the control system 5 (e.g. by the control subsystem 51). FIG. 6 shows a graph comparing the drive frequency (the broken line) with the pump frequency (the solid line) with respect to time.

As will be appreciated, many of the operations of the processing system 4 are operations on the sensor information in the frequency domain. In some embodiments, the sensor information is divided by the processing system 4 in the time domain and one or more harmonic signatures are generated by the processing system 4—e.g. using statistical analysis. The or each harmonic signature may represent the time period that each harmonic occurred in the sensor information. The processing system 4 may be configured to determine a status or imminent event in by comparing the or each harmonic signature with one or more harmonic signatures stored in the archive 41 and associated with known statuses or events. For example, the processing system 4 may generate a histogram of harmonic frequency or number versus the number of occurrences to provide the harmonic signature.

Figure 7:
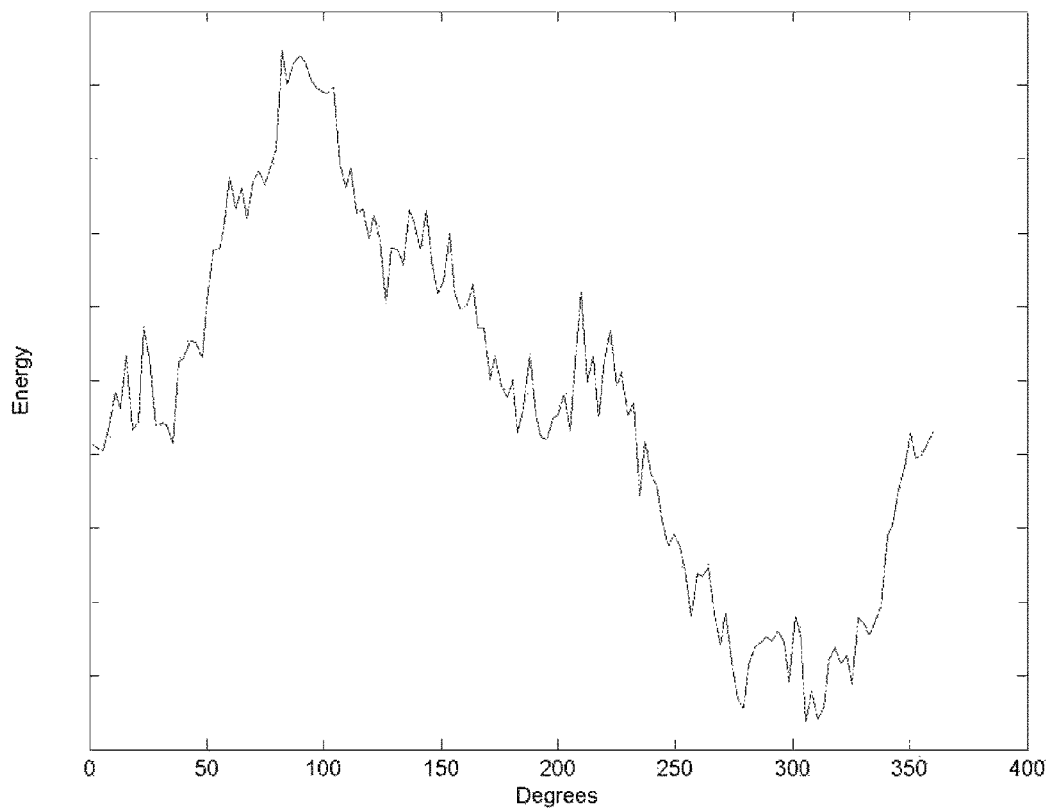
FIG. 7 shows a graph of vibration energy and rotational position of a part of a pump according to some embodiments.

The processing system 4 may be further configured, in the time domain, to generate a representation, which may be a graphical representation, of the vibration amplitude/magnitude at various operating conditions of the one or more items of the equipment 6 (e.g. the pump 61). The operating conditions may be an angular position of a part of the pump 61, for example. This representation may be compared to historic representations stored in the archive 41 to determine a status or imminent event. The processing system 4 may also or alternatively analyse this representation to identify a point source for the vibration. A graphical representation of such information is shown, as an example, in FIG. 7. In FIG. 7, the energy associated with the vibrations is plotted against the angular position of a part of the pump 61. Such a graphical representation may be displayed on the display 42 by the processing system 4.

In some embodiments, changes in frequency spectra or in other data obtained from the sensor information may be detected using changepoint or Bayesian analysis. This analysis may be performed by the processing system 4.

In some embodiments, statistical models for likely variations in the data obtained from the sensor information may be used to determine when the data falls outside of expected minor variations and constitutes a change.

For example, in accordance with a changepoint analysis, the data (obtained from the sensor information) is segmented, and the processing system 4 then determines when a changepoint has occurred by fitting the data to a set of data models and determining when data no longer statistically fits with one of the models. The segmented data may be used to identify what model the current data fits with and the previous model, the new model and/or the changepoint may be used to determine operation characteristics of the one or more items of the equipment 6 (e.g. the pump 61).

Similarly Bayesian analysis of data (obtained from the sensor information) may be used by the processing system 4 to determine properties of operation of the one or more items of the equipment 6 (e.g. the pump 61).

In some embodiments, changes in data obtained from the sensor information which are detected by the processing system 4 may be detected during operation of the one or more items of the equipment 6 (e.g. the pump 61). A change may trigger an audible and/or visual alarm (e.g. via the display 42) which may be presented to the operator.

In some embodiments, changes in the data obtained from the sensor information which are detected by the processing system 4 cause the processing system 4 to send control information to the control system 5 to control the operation of an aspect of the one or more items of equipment 6 (e.g. the pump 61).

In some embodiments, the processing system 4 is configured to use the sensor information to optimise the operation of one or more items of the equipment 6 (e.g. the pump 61). For example, the processing system 4 may be configured to provide the sensor information or a part thereof as feedback to a control algorithm used to control the operation of one or more items of the equipment 6 (e.g. the pump 61). The control algorithm may be part of a control subsystem 51 of the control system 5 or the control subsystem 51 may be part of the processing system 4—which may then send control information to the control system 5 in order to control the one or more items of the equipment 6 (e.g. the pump 61).

The processing system 4 or control system 5 may be further configured to use the auxiliary sensor information as feedback to the control algorithm.

Accordingly, the control algorithm may be configured to control the operation of the one or more items of equipment 6 (e.g. the pump 61) to achieve the desired operation (as may be determined by scrutiny of the auxiliary sensor information) whilst also achieving a desired vibration characteristic—e.g. to minimise vibrations at one or more frequencies, to keep vibrations at one or more frequencies below a predetermined amplitude, or to achieve a predetermined vibration frequency spectrum (e.g. one which is indicative of efficient operation).

In some embodiments, the control algorithm is configured to control the one or more items of the equipment 6 (e.g. the pump 61) by controlling the operation of the Variable Speed Drive 62, if provided.

Thus embodiments may seek to optimise the efficient operation of one or more of the items of the equipment 6 (e.g. the pump 61) and/or the runtime of one or more of the items of the equipment 6 (e.g. the pump 61).

In accordance with some embodiments including the Variable Speed Drive 62, the one or more items of the equipment 6 (e.g. the pump 61) which may be driven by the Variable Speed Drive 62 are driven during a test period through a range of different drive frequencies. During the test period, the sensor system 3 may be configured to provide sensor information to the processing system 4. The processing system 4 may, therefore, be configured to associate different sensor information with different drive frequencies.

In accordance with some embodiments, the processing system 4 may be configured to map sensor information to drive frequency. Thus, the processing system 4 may be configured to correlate information indicative of detected vibrations to drive frequencies.

The processing system 4 may be further configured to determine an optimised drive frequency to achieve a desired vibration characteristic—e.g. to minimise vibrations at one or more frequencies, to keep vibrations at one or more frequencies below a predetermined amplitude, or to achieve a predetermined vibration frequency spectrum (e.g. one which is indicative of efficient operation).

In some embodiments, the test period occurs during installation of the one or more items of the equipment 6 (e.g. the pump 61). In some embodiments, the test period occurs when there is a change in operating parameters associated with the one or more items of the equipment 6 (e.g. the pump 61) and/or the borehole or other conduit 2.

In some embodiments, the test period may occur periodically during operation of the one or more items of the equipment 6 (e.g. the pump 61).

In some embodiments, the processing system 4 may be configured to analyse received sensor information to determine a likely or imminent gas locking event. Such events are a particular problem for downhole and subsea pumps 61.

In response to a gas locking event, one or more of the operating characteristics of the pump 61 should be altered in order to reduce the risk of damage or adverse operation.

The processing system 4 may be configured to detect a likely or imminent gas locking event by comparison of sensor information to historic sensor information known to relate to a gas locking event, and/or to information obtained from models of vibration during a gas locking event. As mentioned above, the processing system 4 may also be configured to use a frequency spectrum (or frequency spectra) to determine a gas locking event.

The processing system 4 may be configured to provide control information to the control system 5 automatically in response to a detected likely or imminent gas locking event, the control information being configured to control the operation of the pump 61 to reduce adverse effects of a gas locking event (by altering the one or more operating characteristics of the pump 61 such as its speed). In some embodiments, the processing system 4 is configured to display a warning on the display 42 or to prompt the operator to cause the transmission of the control information to the control system 5.

In some embodiments, the processing system 4 stores historic sensor information in the archive 41. This historic sensor information represents historic information regarding vibrations detected by the sensor system 3 and, in particular, by the vibration sensor subsystem 31. The historic sensor information may be stored in association with an identifier for one or more of the items of the equipment 6 (e.g. the pump 61) to which the sensor information relates. The vibration information relating to one or more items of the equipment 6 represents a record of the operation of the one or more items of the equipment 6.

The processing system 4 may, therefore, be configured to output a report (e.g. on the display 41) which represents the stored sensor information for the one or more items of the equipment 6.

The processing system 4 may be further configured to receive maintenance information in relation to the one or more items of the equipment 6 (e.g. the pump 61). The maintenance information may be provided in association with the identifier for the one or more items of the equipment 6 and may provide indications of the time and/or nature of maintenance and repair tasks performed in relation to the one or more items of the equipment 6. The processing system 4 may be configured to store the maintenance information in the archive 41 in association with the corresponding sensor information. The processing system 4 may be configured to compare the maintenance information with the stored sensor information in order to identify correlations. For example, the processing system 4 may be configured to identify one or more patterns of sensor information (i.e. patterns of vibration information) preceding a maintenance task.

The processing system 4 may be further configured to identify sensor information (i.e. vibration information) which is associated with one or more items of the equipment 6 which appear to have a long runtime and which appear to have a short runtime between maintenance tasks. This may be used by the processing system 4 to identify vibration characteristics (e.g. a vibration frequency spectrum or spectra) which appear to correspond with long runtimes between maintenance tasks. These vibration characteristics can then be used as target desired vibration characteristics in accordance with embodiments as described herein. Similarly, a frequency spectrum or frequency spectra which are determined by the processing system 4 to be indicative of a status or likely event can be used by embodiments as described herein.

In some embodiments, the processing system 4 is configured to assign one or more values to the identified wear or damage of one or more items of equipment 6 or a component thereof (as determined by analysis of the sensor information). The one or more values may include a first value representative of the difficulty and/or cost of repairing and/or replacing the one or more items of the equipment 6 (such as the pump 61). The one or more values may include a second value representative of issues caused or likely to be caused by failure of the one or more items of equipment 6 (e.g. the pump 61) or a component thereof and/or the effect of reduced function of the one or more items of the equipment 6 (e.g. the pump 61) or a component thereof. The first and/or second value may be representative of a monetary cost.

The processing system 4 may be configured to compare the first value and the second value. The processing system 4 may be configured to use the comparison to determine whether or not repair or replacement of the one or more items of equipment 6 (e.g. the pump 61) or a component thereof is worthwhile and/or beneficial. In some embodiments, the processing system 4 is configured to output this information to the display 42.

In some embodiments, the second value is representative of the effect of down-rating or otherwise operating the one or more items of the equipment 6 (e.g. the pump 61) differently in order to increase run time and/or lifetime of the one or more items of equipment 6 or a component thereof (e.g. representative of a reduced fluid flow rate through the pump 61).

In some embodiments, the processing system 4 determines a third value which may represent the benefit of an increased run time and/or lifetime (e.g. the cost saving in maintenance and repair). The processing system 4 may be configured to compare the second value and the third value. The processing system 4 may be configured to use the comparison to determine whether or not the down-rating or different operation of the one or more items of equipment 6 (e.g. the pump 61) or a component thereof is worthwhile and/or beneficial. In some embodiments, the processing system 4 is configured to output this information to the display 42.

In some embodiments, the processing system 4 is configured to receive sensor information in relation to one or more items of the equipment 6 through or past which fluid is flowing. In a borehole or other conduit 2 (particular in a subsea environment), gases in the fluid will change in volume as they pass through the borehole or other conduit 2 past or through the one or more items of equipment 6.

These gases can cause problems in the operation of the one or more items of equipment 6.

In an example, the one or more items of equipment 6 may include a pump 61 which comprises a plurality of pump stages. The volume of the gases may change as the gases pass through the pump stages of the pump 61.

The processing system 4 may be configured to analyse the sensor information to determine the effect of the increasing volume of the gases on vibration in the pump stages. The processing system 4 may be configured to determine the likely effect of the gases on vibration in one or more downstream pump stages based on the effect measured in relation to one or more upstream pump stages.

In some embodiments, the processing system 4 is configured to output sensor information as an audio signal. The audio signal may be output to a sound output device—such as a speaker or headphones—so that an operator can listen to the sensor information. In this regard, the processing system 4 may be configured to perform one or more signal processing operations on the sensor information in order to generate the audio signal. The one or more signal processing operations may include one or more of filtering the sensor information and amplifying the information. The filtering may include low pass filtering, high pass filtering, and/or band pass filtering. The operator may be able to use the audio signal to identify a status or imminent event in relation to the one or more items of the equipment 6 (e.g. the pump 61).

The processing system 4 may be configured to output control information to the control system 5 to control the operation of one or more downstream pump stages based on the sensor information obtained in relation to the one or more upstream pump stages. This control information may instruct the control system 5 to control one or more of the pump speed, and/or production rate/choke pressure, to mitigate the effects of the gases.

In some embodiments, the control information is determined in order to seek to achieved a desired vibration characteristic in the one or more downstream pump stages of the pump 61.

In some embodiments, the sensor information may be used by the processing system 4 to monitor the progression of gases (e.g. transient gas or a gas slug) through pump stages of the pump 61 (or through or past other items of the equipment 6). This may be achieved by the processing system 6 receiving sensor information associated with the pump stages and comparing the sensor information to modelled information or historic information or by tracking a change in the sensor information representing, for example, increased vibration as the gases move along the pump stages. This information may be displayed on the display 42 to an operator, for example.

In accordance with some embodiments, the processing system 4 may be configured to determine the location along the borehole or other conduit 2 of a liquid-gas interface. The processing system 4 may be configured to receive sensor information relating to a plurality of sensor locations along a length of the borehole or other conduit 2. The processing system 4 may configured to determine changes in the damping or reflections of vibrations represented by the sensor information to determine the location of the gas-liquid interface.

In a more particular example, a pump 61 may be operated in relation to a borehole 22 with a gas-liquid separator, gas is typically placed in an annulus above the pump 61 (for a non-subsea pump). In some embodiments of the present disclosure, the sensor information may be used to determine the location of the gas-liquid interface by identifying reflections and differences in damping between liquid and gas. This identified location (as determined by the processing system 5) may be used to optimize separator efficiency, flow rate and energy consumption—e.g. by the processing system 4 outputting control information to the control system 5 accordingly. Periodic or substantially continuous determining of the liquid-gas interface may also be used by the processing system 5 as an indicator of the rate of gas accumulation in the annulus. As such, the processing system 4 may be used as a simple multiphase flow meter and may output flow information on the display 42.

In another specific example, shale gas wells are dewatered by intermittently running the pump 61 in the borehole 21. In such operations, there is a risk of pumping the well dry and damaging the pump 61. It is also beneficial to minimise the number of start-up events to reduce stress on the pump 61. Accordingly, the processing system 4 may detect the liquid-gas interface and then send control information to the control system 5 to operate the pump 61 when necessary, such that the well is not pumped dry.

In some embodiments, the sensor information is analysed by the processing system 4 to determine likely sand production rates within a borehole 21—as this has an effect on vibration. The processing system 4 may be configured to output control information to the control system 5 to control the operation of the pump 61 (and/or one or more other items of the equipment 6) to minimise sand production rates or to keep sand production rates below a predetermined level.

In some embodiments, the vibration effect caused by the production of sand is increased by providing one or more flow directors 611 on a surface of one or more of the items of equipment 6 (such as the pump 61) to generate turbulent flow and/or to alter the flow. The one or more flow directors 611 may include a rough surface and/or a vortex shedding element.

In accordance with some embodiments, an active sensing method is used in which the pump 61 is driven (as a result of control information sent to the control system 5 by the processing system 4) to create one or more pulses of fluid within the borehole or other conduit 2. The processing system 4 may then use the sensor information to track the pulse along a length of the borehole or other conduit 2. The processing system 4 may be configured to determine flow rate or flow regime information appurtenant to the pump 61.

In some embodiments, the processing system 4 may be configured to receive the temperature information which is output by some example embodiments of the sensor system 3. The processing system 4 may be further configured to determine the temperature (or a parameter indicative of the temperature) at one or more locations along a length of the electrical power transmission cable 63. The processing system 4 may be configured to identify the presence of any hot spots indicated in the temperature information and/or likely areas of water ingress. The processing system 4 may be configured to output information concerning any hotspots and water ingress (e.g. that there are such hotspots or water ingress, the location thereof, and the temperature of the cable 63 at one or more locations along its length) to the display 42 for presentation to the operator.

As will be appreciated, the processing system 4 operates on the sensor information primarily in the frequency domain (see some exceptions mentioned above). This avoids issues caused by the constructive or destructive interference which would be observed in the time domain.

In accordance with some embodiments, the processes of the processing system 4 are configured to operate on frequency domain information associated with regions of the borehole or other conduit 2 and/or with parts of the one or more items of the equipment 6 (e.g. the pump 61). Thus, for example sensor information from a plurality of sensor locations for one region may be summed in the frequency domain. This summation may be weighted in favour of the sensor locations towards the centre of the region—to reduce edge effects.

In some embodiments, the regions are selected in accordance with a scale—e.g. every 1 m, every 50 cm, every 10 cm, etc. In other embodiments, the regions are selected due to their association with a part of the one or more items of the equipment 6 (e.g. the pump 61) so that the vibrations associated with that part may be analysed—e.g. to identify a status or imminent event in relation to that part.

As will be appreciated, in accordance with some embodiments, therefore, the processing system may be configured to process the received sensor information to determine one or more parameters, signatures, frequency spectra, and the like which are indicative of:

a. the flow of fluid through the one or more items of the equipment 6 (such as the pump 61), and/or
b. an operating characteristic of the one or more items of the equipment 6 (e.g. the pump 61), and/or
c. the flow of fluid through the one or more items of the equipment 6 (such as the pump 61), and/or
d. the fluid which has been pumped by the pump 61, and/or
e. the flow of fluid upstream and/or downstream of the one or more items of the equipment 6 (such as the pump 61).

In other words, the sensor information is used to determine one or more characteristics which are representative of the operation of the one or more items of the equipment 6 and/or the borehole or other conduit 2. This may include the conduit thereof.

The processing system 4 may then use this information as the basis of the issuance of one or more control instructions to the control system 5.

As will be appreciated, embodiments of the present disclosure may be utilised during one or more of start-up, shutdown, and/or production operations associated with a borehole or other conduit 2—particularly in hydrocarbon exploration and extraction.

Embodiments may seek to prolong the total runtime (i.e. the lifetime) of one or more items of the equipment 6 (such as the pump 61) and to monitor the health thereof.

Embodiments of the present disclosure may seek to provide a monitoring system in which vibration can be monitored at several kHz, in substantially realtime, and along the length of one or more of the items of the equipment 6 (such as the pump 61), independent of other telemetry for the one or more items of equipment 6. This monitoring system 1 may be configured to monitor production under the pump 61 and/or to detect leaking in the completion.

As will be understood, the sensor information is indicative of vibrations at the sensor locations and is, more specifically, indicative of changes in the strain on—for example—one or more optical fibres 311 at the sensor locations. The sensor information may also be described as representing one or more acoustic events.

For the purposes of explanation, the parts of embodiments of the present disclosure have been separated into various systems and subsystems—e.g. the monitoring system 1, the sensor system 3, the vibration sensor subsystem 31, the processing system 4, and the control system 5. It will be appreciated that the operations of each system and subsystem as described herein may be undertaken by different systems (i.e. by different systems or subsystems). In addition, each system or subsystem may comprise a plurality of parts. For example, the processing system 4 may comprise a plurality of modules configured to perform the various processes described herein. The implementation of those processes may be spread over a distribution computing system or may be undertaken by a single computing device.

The above description provides preferred exemplary embodiments only, and is not intended to limit the scope, applicability or configuration of the invention. Rather, the description of the preferred exemplary embodiments will provide those skilled in the art with an enabling description for implementing a preferred exemplary embodiment of the invention—it being understood that various changes may be made in the function and arrangement of elements without departing from the spirit and scope of the invention as set forth in the appended claims.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

As will be appreciated, the pump 61 may comprise a plurality of pump stages and the pump 61 (or each of the pump stages) may include a plurality of components such as one or more motors, valves, electric control systems, blades, housings and the like.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A monitoring system for one or more items of equipment associated with a borehole or other conduit, the monitoring system comprising:
    a sensor system having a vibration sensor subsystem which is configured to output sensor information indicative of vibrations at one or more sensor locations, the one or more sensor locations being associated with the one or more items of equipment and/or fluid flow within the borehole or other conduit; and
    a processing system which is configured to:
        process the sensor information to determine a characteristic of the operation of the one or more items of equipment and/or the fluid flow within the borehole or other conduit, the characteristic including a frequency spectrum of the vibrations at the one or more sensor locations summed over a monitoring time period;
        identify one or more changes in the characteristic indicative of a status or imminent event based on comparing the frequency spectrum with one or more historic frequency spectra summed over a time period and thereby determining the status or the imminent event in relation to the one or more items of equipment, and
        output control information to control the operation of the one or more items of equipment responsive to the identified one or more changes.

2. The monitoring system of claim 1, wherein the control information includes an instruction to shut down, start-up, slow down, or speed up the one or more items of equipment.

3. The monitoring system of claim 1, wherein the status or the imminent event includes one or more of: a failure of the one or more items of equipment, an imminent failure of the one or more items of equipment, inefficient operation of the one or more items of equipment, or damage to part of the one or more items of equipment.

4. The monitoring system of claim 1, wherein the processing system is further configured to determine a plurality of frequency spectra, with each frequency spectrum relating to and summed over a different monitoring time period, and to analyse the plurality of frequency spectra to identify one or more changes in the frequency spectra.

5. The monitoring system of claim 4, wherein the one or more changes in the frequency spectra include a change of frequency of vibrations and/or a change of amplitude or magnitude of vibrations.

6. The monitoring system of claim 1, wherein the plurality of frequency spectra, or each spectrum, is generated using sensor information from a plurality of the one or more sensor locations, wherein the sensor information has been summed in a frequency domain to produce a summation.

7. The monitoring system of claim 6, wherein the summation is a weighted summation based on the position of the one or more sensor locations relative to a center of a region.

8. The monitoring system of claim 1, wherein the characteristic includes one or more harmonic frequencies of vibration.

9. The monitoring system of claim 8, wherein the processing system is further configured to compare the one or more harmonic frequencies with one or more historic harmonic frequencies to determine the status or the imminent event in relation to the one or more items of equipment.

10. The monitoring system of claim 1, wherein the characteristic includes a liquid-gas interface location.

11. The monitoring system of claim 1, wherein the characteristic includes a sand production rate.

12. The monitoring system of claim 1, wherein the characteristic is an indication of gases in fluid passing through or past the one or more items of equipment.

13. The monitoring system of claim 1, wherein determining a characteristic of the operation of the one or more items of equipment and/or the fluid flow within the borehole or other conduit includes outputting an audio signal representative of vibrations at the one or more sensor locations.

14. The monitoring system of claim 1, wherein the one or more items of equipment includes a pump and the one or more sensor locations are associated with the pump.

15. The monitoring system of claim 14, wherein the pump is an electrical submersible pump.

16. The monitoring system of claim 1, wherein the vibration sensing subsystem includes one or more optical fibers and the one or more sensor locations are locations along a length of the one or more optical fibers.

17. The monitoring system of claim 16, wherein the vibration sensor subsystem is a distributed vibration sensor.

18. The monitoring system of claim 17, wherein the distributed vibration sensor is a heterodyne distributed vibration sensor.

19. The monitoring system of claim 16, wherein the vibration sensor subsystem includes:

an electromagnetic radiation source configured to emit electromagnetic radiation along the optical fiber and located at a first location; and an electromagnetic radiation receiver configured to receive electromagnetic radiation reflected towards the first location by the optical fiber or one or more other components of the vibration sensor subsystem.

20. The monitoring system of claim 16, wherein the vibration sensor subsystem is configured to output temperature sensor information indicative of a temperature at the one or more sensor locations.

21. The monitoring system of claim 16, wherein the vibration sensor subsystem includes at least one Bragg grating at the one or more sensor locations.

22. The monitoring system of claim 16, further comprising:

one or more switches or filters that obtain temperature and vibration data over the same one or more optical fibers by modulating operation of the vibration sensor subsystem over time or wavelength.

23. The monitoring system of claim 1, wherein the vibration sensor subsystem is further configured to output sensor information indicative of vibrations at the one or more sensor locations caused as the result of the operation of the one or more items of equipment in accordance with the control information.

24. The monitoring system of claim 1, further comprising an auxiliary sensor subsystem which is configured to output auxiliary sensor information to the processing system, the auxiliary sensor information being indicative of an aspect of the operation of the one or more items of equipment, wherein the processing system is further configured to determine the characteristic based on the sensor information and the auxiliary sensor information.

25. The monitoring system of claim 1, wherein the characteristic of the one or more items of equipment and/or the fluid flow within the borehole or other conduit includes a flow condition for fluid upstream or downstream of the one or more items of equipment.

26. The monitoring system of claim 1, wherein the processing system is further configured to prompt the operator automatically to schedule maintenance as a result of the identified one or more changes.

27. A method of monitoring one or more items of equipment associated with a borehole or other conduit, the method comprising:

outputting sensor information indicative of vibrations at one or more sensor locations, the one or more sensor locations being associated with the one or more items of equipment and/or fluid flow within the borehole or other conduit; and processing the sensor information to:

generating a frequency spectrum by summing the sensor information indicative vibrations at the one or more sensor locations over a monitoring time period;

determine a characteristic of the operation of the one or more items of equipment and/or the fluid flow within the borehole or other conduit, identify one or more changes in the characteristic indicative of a status or imminent event based on comparing the frequency spectrum with noe or more historic frequency spectra summed over a time period and thereby determining the status or the imminent event in relation to the one or more items of equipment, and output control information to control the operation of the one or more items of equipment responsive to the identified one or more changes.

28. The method of claim 27, wherein the control information includes an instruction to shut down, start-up, slow down, or speed up the one or more items of equipment.

29. The method of claim 27, wherein the status or the imminent event includes one or more of: a failure of the one or more items of equipment, an imminent failure of the one or more items of equipment, inefficient operation of the one or more items of equipment, or damage to part of the one or more items of equipment.

30. The method of claim 27, further comprising:
determining a plurality of frequency spectra, with each frequency spectrum relating to and summed over a different monitoring time period; and
analyzing the plurality of frequency spectra to identify one or more changes in the frequency spectra.

31. The method of claim 30, wherein the one or more changes in the frequency spectra include a change of frequency of vibrations and/or a change of amplitude or magnitude of vibrations.

32. The method of claim 27, further comprising:
generating the plurality of frequency spectra, or each spectrum, using sensor information from a plurality of the one or more sensor locations, wherein the sensor information has been summed in a frequency domain to produce a summation.

33. The method of claim 32, wherein the summation is a weighted summation based on the position of the one or more sensor locations relative to a center of a region.

34. The method of claim 27, wherein the characteristic includes one or more harmonic frequencies of vibration.

35. The method of claim 34, further comprising:
comparing the one or more harmonic frequencies with one or more historic harmonic frequencies to determine the status or the imminent event in relation to the one or more items of equipment.

36. The method of claim 27, wherein the characteristic includes a liquid-gas interface location.

37. The method of claim 27, wherein the characteristic includes a sand production rate.

38. The method of claim 27, wherein the characteristic is an indication of gases in fluid passing through or past the one or more items of equipment.

39. The method of claim 27, wherein processing the sensor information to determine a characteristic of the operation of the one or more items of equipment and/or the fluid flow within the borehole or other conduit includes outputting an audio signal representative of vibrations at the one or more sensor locations.

40. The method of claim 27, wherein the one or more items of equipment includes a pump and the one or more sensor locations are associated with the pump.

41. The method of claim 40, wherein the pump is an electrical submersible pump.

42. The method of claim 27, wherein the one or more sensor locations are locations along a length of one or more optical fibers.

43. The method of claim 42, wherein the vibration sensor subsystem is a distributed vibration sensor.

44. The method of claim 43, wherein the distributed vibration sensor is a heterodyne distributed vibration sensor.

45. The method of claim 27, further comprising:
emitting electromagnetic radiation along an optical fiber from a first location; and
receiving electromagnetic radiation reflected towards the first location by the optical fiber or one or more other components of a vibration sensor subsystem.

46. The method of claim 27, further comprising:
outputting temperature sensor information indicative of a temperature at the one or more sensor locations.

47. The method of claim 27, further comprising:
outputting sensor information indicative of vibrations at the one or more sensor locations caused as the result of the operation of the one or more items of equipment in accordance with the control information.

48. The method of claim 27, further comprising:
outputting auxiliary sensor information indicative of an aspect of the operation of the one or more items of equipment, and
determining the characteristic includes determining the characteristic based on the sensor information and the auxiliary sensor information.

49. The method of claim 27, wherein the characteristic of the one or more items of equipment and/or the fluid flow within the borehole or other conduit includes a flow condition for fluid upstream or downstream of the one or more items of equipment.

50. The method of claim 27, wherein the processing is further to prompt the operator automatically to schedule maintenance as a result of the identified one or more changes.

51. The method of claim 27, generating the frequency spectrum including summing sensor information from a same one of the one or more sensor locations over the monitoring time period.

52. The method of claim 27, wherein outputting control information is part of an active sensing system that controls changes of the one or more items of equipment and changes vibrations at the one or more sensor locations to a predetermined vibration signature.

* * * * *